United States Patent [19]

Nakagawa et al.

[11] 4,022,784
[45] May 10, 1977

[54] 5-[1-HYDROXY-2-(SUBSTITUTED-AMINO)-]ALKYL-8-SUBSTITUTED-CARBOSTYRIL AND -3,4-DIHYDROCARBOSTYRIL DERIVATIVES

[75] Inventors: Kazuyuki Nakagawa, Tokushima; Shiro Yoshizaki, Naruto; Kaoru Tanimura; Shigeharu Tamara, both of Tokushima, all of Japan

[73] Assignee: Otsuka Pharmaceutical Company Limited, Tokyo, Japan

[22] Filed: Dec. 26, 1974

[21] Appl. No.: 536,703

[30] Foreign Application Priority Data

Nov. 8, 1974 Japan .............................. 49-129381
Nov. 8, 1974 Japan .............................. 49-129382
Nov. 8, 1974 Japan .............................. 49-129383
Nov. 8, 1974 Japan .............................. 49-129384
Nov. 11, 1974 Japan .............................. 49-130726
Nov. 11, 1974 Japan .............................. 49-130727
Nov. 11, 1974 Japan .............................. 49-130729

[52] U.S. Cl. .................... 260/288 R; 260/247.2 A; 260/268 BQ; 260/289 K; 424/248.57; 424/250; 424/248.58; 424/258
[51] Int. Cl.² ............ C07D 215/26; C07D 215/22
[58] Field of Search ... 260/288 R, 288 CE, 247.2 A, 260/268 BQ

[56] References Cited

UNITED STATES PATENTS 3,555,030  1/1971  Loev et al. .................... 260/289 K

FOREIGN PATENTS OR APPLICATIONS 959,918  4/1950  France .................... 260/288 R
2,261,506  6/1973  Germany .................... 260/268 R

OTHER PUBLICATIONS

Morrison et al; Organic Chemistry; (1969); p. 666.
Chodnehar et al; J. Med. Chem.; vol. 15; pp. 49–57, 1972.
Morrison et al; Org. Chem.; (1969) p. 866.
Morrison et al; Org. Chem.; (1969) p. 177.
Burst et al; Arch. Int. Pharmacodyn. vol. 209 (1974) pp. 227–236.
Cantarelli et al., Chem. Abs., vol. 67, 2958a (1967).
Chem. Abs., vol. 62:16212e (abstract of Neth. Appl. 6,405,107) 1965.
Chem. Abs. vol., 81:3968e (1974).

Primary Examiner—Donald G. Daus
Assistant Examiner—Mary C. Vaughn
Attorney, Agent, or Firm—Sughrue, Rothwell, Mion, Zinn & Macpeak

[57] ABSTRACT

5-[1-Hydroxy-2-(substituted-amino)]alkyl-8-substituted-carbostyril derivatives and 5-[1-hydroxy-2-(substituted-amino)]-alkyl-8-substituted-3,4-dihydrocarbostyril derivatives represented by the formulas (Ia) and (Ib)

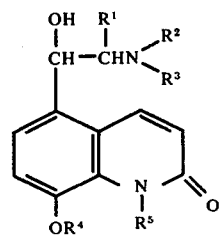

(Ia)

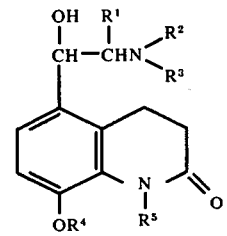

(Ib)

wherein $R^1$, $R^4$ and $R^5$ each represents a hydrogen atom or an alkyl group having 1 to 4 carbon atoms, with at least one of $R^4$ and $R^5$ being an alkyl group, and $R^2$ and $R^3$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6-membered substituted or unsubstituted heterocyclic ring containing 1 or 2 nitrogen, oxygen or sulfur atoms as hetero atoms, the pharmaceutically acceptable acid addition salts thereof, and a process for preparing the same.

6 Claims, No Drawings

5-[1-HYDROXY-2-(SUBSTITUTED-AMINO)]AL-KYL-8-SUBSTITUTED-CARBOSTYRIL AND -3,4-DIHYDROCARBOSTYRIL DERIVATIVES

BACKGROUND OF THE INVENTION

1. Field of the Invention

This invention relates to a novel carbostyril derivative and a process for preparing the same. More particularly, this invention relates to novel 5-[1-hydroxy-2-(substituted-amino)]alkyl-8-substituted-carbostyril derivatives, 5-[1-hydroxy-2-(substituted-amino)]alkyl-8-substituted-3,4-dihydrocarbostyril derivatives, the pharmaceutically acceptable acid addition salts thereof, and a process for preparing the same.

2. Description of the Prior Art

It is well known that certain carbostyril derivatives exhibit useful pharmaceutical activities. Representative compounds of this type have been disclosed in *Journal of Medical Chemistry*, Vol. 15, No. 3, pp.260–266 (1972), Japanese Patent Publication No. 38789/1971 and *Chemical Abstracts*, 62, 16212e (1965), etc. However, these prior art references do not teach that the compounds having a [1-hydroxy-2-(substituted-amino)]alkyl group at the 5-position of the carbostyril or 3,4-dihydrocarbostyril moiety possess an excellent β-adrenoreceptor stimulating activity.

It has now been found that carbostyril and 3,4-dihydrocarbostyril derivatives having a [1-hydroxy-2-(substituted-amino)]-alkyl group at the 5-position and having a substituent at the 1-and/or 8-position of the carbostyril or 3,4-dihydrocarbostyril moiety and the pharmaceutically acceptable acid addition salts thereof possess a β-adreno-receptor stimulating activity and, therefore, are useful as a therapeutic agent such as a bronchodilator, a peripheral vasodilator, an antihypertensive agent and the like, particularly for treating bronchial asthma.

SUMMARY OF THE INVENTION

An object of the present invention is to provide 5-[1-hydroxy-2-(substituted-amino)]alkyl-8-substituted-carbostyril derivatives represented by the formula (Ia)

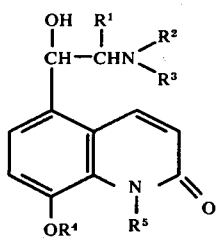

(Ia)

and 5-[1-hydroxy-2-(substituted-amino)]alkyl-8-substituted-3,4-dihydrocarbostyril derivatives represented by the formula (Ib)

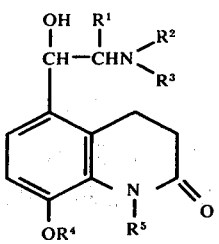

(Ib)

wherein $R^1$, $R^4$ and $R^5$ each represents a hydrogen atom or an alkyl group having 1 to 4 carbon atoms, with at least one of $R^4$ and $R^5$ being an alkyl group, and $R^2$ and $R^3$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6-membered substituted or unsubstituted heterocyclic ring containing 1 or 2 nitrogen, oxygen or sulfur atoms as hetero atoms.

Another object of this invention is to provide a process for preparing the above 5-[1-hydroxy-2-(substituted-amino)]alkyl-8-substituted-carbostyril and 5-[1-hydroxy-2-(substituted-amino)]-alkyl-8-substituted-3,4-dihydrocarbostyril derivatives represented by the formulas (Ia) and (Ib).

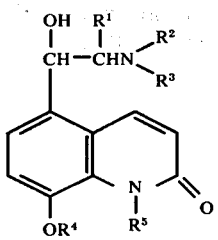

(Ia)

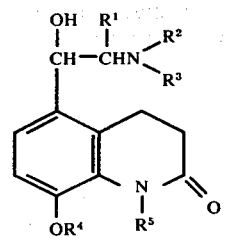

(Ib)

wherein $R^1$, $R^4$ and $R^5$ each represents a hydrogen atom or an alkyl group having 1 to 4 carbon atoms, with at least one of $R^4$ and $R^5$ being an alkyl group, and $R^2$ and $R^3$, which may be the same or different, each represents a hydrogen atom, an alkyl group having 1 to 4 carbon atoms, an aralkyl group containing a straight or branched chain alkyl moiety having 1 to 4 carbon atoms or a cycloalkyl group having 4 to 6 carbon atoms, or $R^2$ and $R^3$ may, when taken together with the nitrogen atom to which they are attached, form a 5- or 6-membered substituted or unsubstituted heterocyclic ring containing 1 or 2 nitrogen, oxygen or sulfur atoms as hetero atoms, and the pharmaceutically acceptable acid addition salts thereof, which comprises the steps of 1. reacting an 8-substituted-carbostyril of the formula (VI)

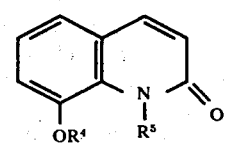

(VI)

wherein $R^4$ and $R^5$ are as defined above, while an α-haloalkanoic acid halide of the formula (V)

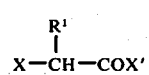

(V)

wherein $R^1$ represents an alkyl group having 1 to 4 carbon atoms; and X and X', which may be the same or different, each represents a halogen atom, to obtain a 5-(α-haloalkanoyl)-8-substituted-carbostyril derivative of the formula (IV)

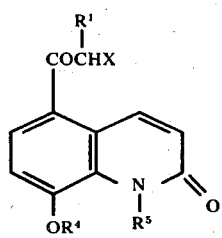

wherein $R^1$, $R^4$, $R^5$ and X are as defined above, 2. reacting the resulting 5-($\alpha$-haloalkanoyl)-8-substituted-carbostyril derivative of the formula (IV) with an amine of the formula (III)

wherein $R^2$ and $R^3$ are as defined above, to obtain a 5-($\alpha$-substituted-aminoalkanoyl)-8-substituted-carbostyril derivative represented by the formula (II)

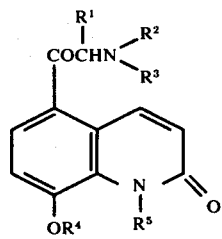

wherein R, $R^1$, $R^2$, $R^3$, $R^4$ and $R^5$ are as defined above, and 3. reducing the resulting 5-($\alpha$-substituted-aminoalkanoyl)-8-substituted-carbostyril derivative of the formula (II) by a catalytic reduction or a reduction using a reducing agent.

The 5-[1-hydroxy-2-(substituted-amino)]alkyl-8-substituted-carbostyril derivatives of the formula (I$a$) and 5-[1-hydroxy-2-(substituted-amino)]alkyl-8-substituted-3,4-dihydrocarbostyril derivatives of the formula (I$b$) and the acid addition salts thereof exhibit a $\beta$-adreno-receptor stimulating activity and, therefore, are useful as a bronchodilator, a peripheral vasodilator or an antihypertensive agent.

DETAILED DESCRIPTION OF THE INVENTION

The term "alkyl" as used herein for $R^1$, $R^2$ $R^3$, $R^4$ and $R^5$ means a straight or branched chain alkyl group having 1 to 4 carbon atoms, and includes, for example, a methyl, ethyl, propyl, isopropyl, butyl, sec-butyl, tert-butyl group and the like.

The term "aralkyl" as used herein means an aralkyl group containing a straight or branched chain alkyl moiety having 1 to 4 carbon atoms, for example, a benzyl, $\alpha$-methylbenzyl, $\alpha,\alpha$-dimethylbenzyl, phenethyl, $\alpha,\alpha$-dimethylphenethyl group and the like.

The term "cycloalkyl" as used herein means a cycloalkyl group having 4 to 6 carbon atoms, for example, a cyclobutyl, cyclopentyl, cyclohexyl group and the like.

The term "5 or 6-membered substituted or unsubstituted heterocyclic ring" as used herein means heterocyclic groups containing 1 or 2 nitrogen, oxygen or sulfur atoms as hetero atoms such as a pyrrolidino, pyrrolidinyl, piperidino, piperidinyl, morpholino, morpholinyl, piperazino, piperazinyl or a like group which can be unsubstituted or substituted with an alkyl group having 1 to 4 carbon atoms, such as a methyl, ethyl, iso-propyl, tert-butyl group and the like, for example, a 2-methylpiperidino, 3-methylpiperidino, N-methylpiperazino group and the like.

The term "halogen" as used herein includes fluorine, chlorine, bromine and iodine, preferably, chlorine and bromine.

The compounds of the present invention represented by the formulae (I$a$) and (I$b$) can be prepared from a starting carbostyril compound of the formula (VI) according to the following reaction schemes:

Reaction Scheme I

Preparation of the compounds of the formulae (I$a$) and (I$b$):

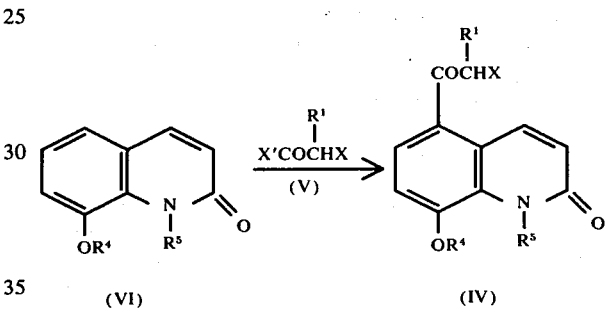

Reaction Scheme II

Preparation of compounds of the formulae (I$a$) and (I$b$) wherein $R^4$ is a hydrogen atom and $R^5$ is an alkyl group:

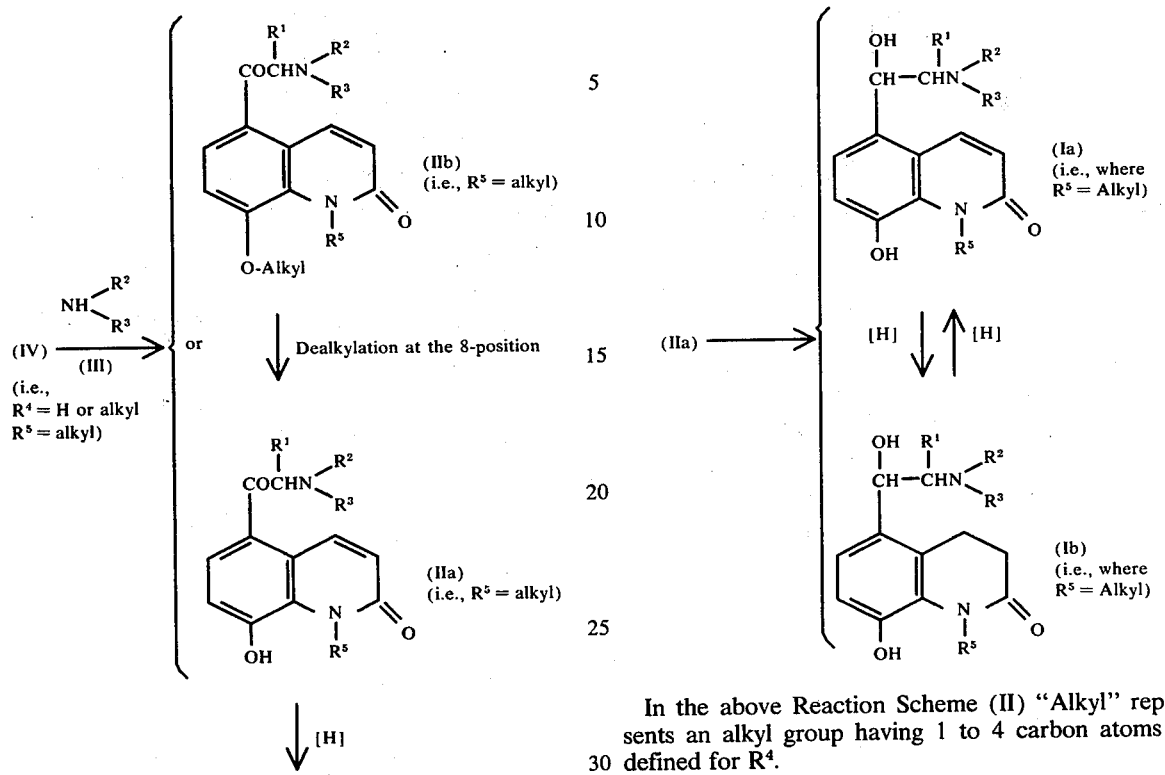

In the above Reaction Scheme (II) "Alkyl" represents an alkyl group having 1 to 4 carbon atoms as defined for $R^4$.

Reaction Scheme III

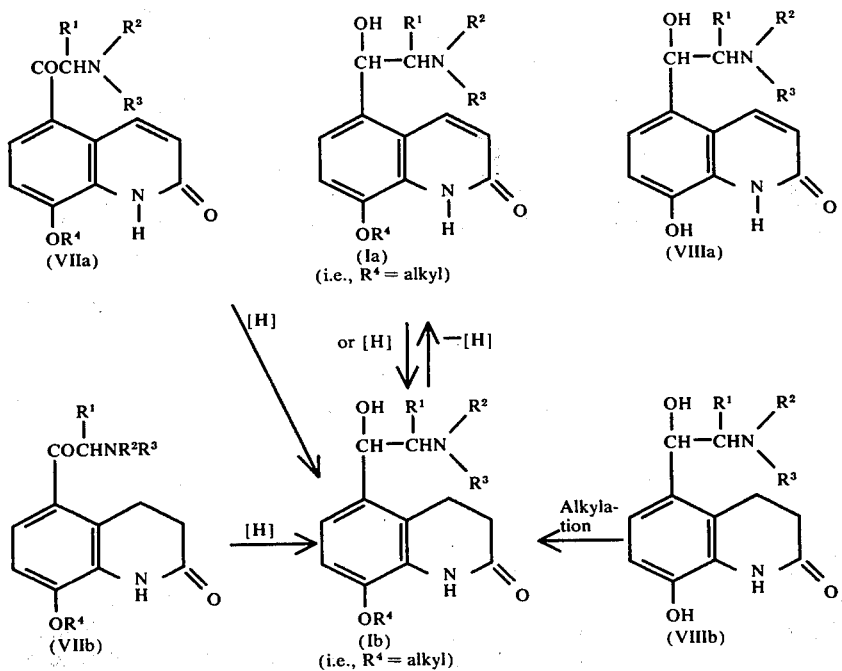

Preparation of the compounds of the formulae (Ia) and (Ib) wherein $R^4$ is an alkyl group and $R^5$ is a hydrogen atom.

According to the process shown in Reaction Scheme I above, the compounds of the present invention represented by the formula (Ia) and (Ib) can be prepared by
1. reacting a carbostyril of the formula (VI)

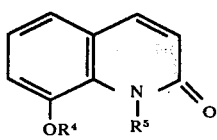

(VI)

wherein $R^4$ and $R^5$ are as defined above, with an α-haloalkanoic acid halide of the formula (V)

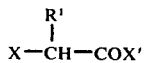

(V)

wherein $R^1$ represents an alkyl group having 1 to 4 carbon atoms; and X and X′, which may be the same or different, each represents a halogen atom, to obtain a 5-(α-haloalkanoyl)carbostyril derivative having the formula (IV)

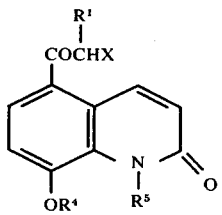

(IV)

wherein $R^1$, $R^4$, $R^5$ and X are as defined above, 2. reacting the resulting 5-(α-haloalkanoyl)-8-substituted-carbostyril derivative of the formula (IV) with an amine of the formula (III)

(III)

wherein $R^2$ and $R^3$ are as defined above, to obtain a 5-(α-substituted-aminoalkanoyl)-8-substituted-carbostyril derivative represented by the formula (II)

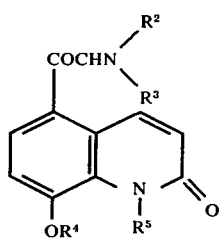

(II)

wherein R, $R^1$, $R^2$, $R^3$, $R^4$ and $R^5$ are as defined above, and 3. reducing the resulting 5-(α-substituted-aminoalkanoyl)-8-substituted carbostyril derivative of the formula (II) with hydrogen by a catalytic reduction or a reduction using a reducing agent.

Further, in the Reaction Scheme II described above, as a result of step (2) using a starting carbostyril of the formula (VI) wherein $R^4$ is a hydrogen atom or an alkyl group and $R^5$ is an alkyl group, a 5-(α-substituted-aminoalkanoyl)-8-hydroxycarbostyril derivative of the formula (IIa)

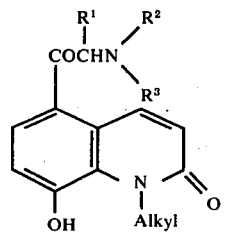

(IIa)

wherein "Alkyl" represents an alkyl group having 1 to 4 carbon atoms as defined for $R^5$ and $R^1$, $R^2$ and $R^3$ are as defined above, or a 5-(α-substituted-aminoalkanoyl)-8-alkoxycarbostyril derivative having the formula (IIb)

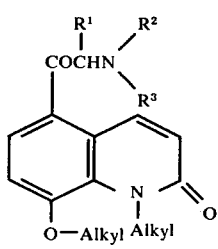

(IIb)

wherein "Alkyl" represents an alkyl group having 1 to 4 carbon atoms as defined for $R^4$ and $R^1$, $R^2$ and $R^3$ are as defined above is produced. Subsequent dealkylation of the alkyl group at the 8-position of the 5-(α-substituted-aminoalkanoyl)-8-alkoxycarbostyril of the formula (IIb) with a hydrogen halide produces the corresponding 8-hydroxycarbostyril having the formula (IIa) which can be reduced in accordance with the procedures described for the reduction of the 5-(α-substituted-aminoalkanoyl)-8-substituted-carbostyril derivative of the formula (II) to produce the 8-hydroxy-substituted-carbostyril derivatives of the formulas (Ia) and (Ib) as described hereinbefore in Reaction Scheme (II).

The 1- and/or 8-substituted-carbostyril (VI) used as a starting material of the present invention is a known compound, and can easily be prepared, for example, by the method as described in George R. Pettit et al, *J. Org. Chem.*, 33, 1089 (1968).

The α-haloalkanoic acid halide of the formula (V) which can be used in this invention includes α-chloropropionyl chloride, α-bromopropionyl chloride, α-chlorobutyryl chloride, α-bromobutyryl chloride, α-bromobutyryl bromide, α-chlorovaleryl chloride and the like.

The reaction between the carbostyril compound of the formula (VI) and the α-haloalkanoic acid halide of the formula (V) can be conducted using a Lewis acid as a catalyst, for example, aluminum chloride, aluminum bromide, zinc chloride, ferric chloride, stannic chloride, boron trifluoride and titanium chloride, in an amount of about 2 to about 10 moles, preferably 3 to 6 moles, per mole of the starting carbostyril (VI). The α-haloalkanoic acid halide of the formula (V) is used in an equimolar amount to a large excess relative to the carbostyril of the formula (VI) but generally in an amount of from about 2 to about 20 moles, most preferably 2 to 10 moles, per mole of the starting carbostyril of the formula (VI). The reaction can be carried out in the absence or presence of an appropriate solvent such as carbon disulfide, nitrobenzene, diethyl ether, dioxane and the like and in the presence of the above enumerated catalyst, advantageously under anhydrous conditions, at room temperature (about 20° to 30° C) to about 150° C, preferably from room temperature to about 80° C for a period of about 1 to about 20 hours, preferably 4 to 10 hours. The above solvent is usually used in a volume of about 0.5 to about 20, preferably 2 to 10, times the volume of the reactants.

The amines of the formula (III) which can be used in the reaction with the 5-(α-haloalkanoyl)-1- and/or -8-substituted carbostyril of the formula (IV) include alkylamines, for example, methylamine, ethylamine, n-propylamine, isopropylamine, n-butylamine, sec-butylamine, tert-butylamine; cyclopentylamine, cyclohexylamine; aralkylamine, for example, benzylamine, α-methylbenzylamine, α,α-dimethylbenzylamine, phenethylamine, α,α-dimethylphenetylamine and the like; and substituted or unsubstituted heterocyclic amine, for example, pyrrolidine, piperidine, morpholine, piperazine, 2-methylpiperidine, 3-methylpiperidine, N-methylpiperazine and the like. of 40° to 100° C, in an appropriate solvent or using the amine of the formula (III) per se as a solvent to obtain a 5-(α-substituted-aminoalkanoyl)-8-substituted-carbostyril of the formula (II), a 1-alkyl-5-(α-substituted-aminoalkanoyl)-8-hydroxycarbostyril of the formula (IIa) or a 1-alkyl-5-(α-substituted-aminoalkanoyl)-8-alkoxycarbostyril of the formula (IIb) as described in Reaction Schemes (I) and (II).

Thus, when the 8-hydroxycarbostyril of the formula (VI) wherein $R^4$ is a hydrogen atom ($R^5$ is alkyl) is used as a starting material, the 1-alkyl-5-(α-substituted-aminoalkanoyl)-8-hydroxycarbostyril of the formula (IIa) is obtained, which can be subjected to the subsequent reduction reaction to produce the 1-alkyl-5-(α-substituted-aminoalkanoyl)-8-hydroxy-3,4-dihydrocarbostyril of the formula (Ib). When the 8-alkoxycarbostyril of the formula (VI) wherein $R^4$ is an alkyl group ($R^5$ is alkyl) is used as a starting material, the corresponding 1-alkyl-5-(α-substituted-aminoalkanoyl)-8-alkoxycarbostyril of the formula (IIb) is obtained. The resulting 1-alkyl-5-(α-substituted-aminoalkanoyl)-8-alkoxy-carbostyril (IIb) is then reacted with a hydrogen halide to dealkylate the 8-position of the carbostyril moiety thereby obtaining the compound of the formula (IIa) which can be subjected to the subsequent reduction described above to produce a compound of the formula (Ib).

The hydrogen halides used in this dealkylation of the alkoxy group at the 8-position include, for example, hydrogen bromide, hydrogen chloride, hydrogen iodide and the like, preferably, hydrogen bromide. These hydrogen halides can advantageously be employed in an appropriate solvent such as methanol, ethanol, propanol, preferably water, in a form of an aqueous solution of the hydrogen halide in a concentration of about 10 to 50%, preferably 47% hydrogen bromide.

This dealkylation reaction of the alkoxy group at the 8-position can generally be carried out using the hydrogen halide in an equimolar amount, preferably, a large excess with respect to the compound of the formula (IIb) by heating to a temperature of from about 100° to about 150° C, preferably at the refluxing temperature, for about 1 to about 20 hours, preferably 3 to 10 hours.

The reduction of the 5-(α-substituted-aminoalkanoyl)-8-substituted-carbostyril of the formula (II) to the compounds of the present invention represented by the formula (Ia) can be conducted by a conventional reduction using a reducing agent such as lithium aluminum hydride, sodium borohydride and the like, or a conventional catalytic reduction in the presence of a catalyst such as palladium black, palladium-on-carbon, Raney nickel, platinum black, platinum oxide and the like and hydrogen.

The above reducing agent can be used in an amount of from about 2 to about 10 moles, preferably 2 to 5 moles, per mole of the carbostyril compound of the formula (II) in a solvent while cooling under atmospheric pressure at a temperature of from about 0° to about 100° C, preferably 20° to 50° C. When sodium borohydride is used as a reducing agent, the solvent is preferably water or alcohols such as methanol, ethanol and the like, and when lithium aluminum hydride is used as a reducing agent, the solvent is preferably a non-aqueous solvent such as anhydrous diethyl ether, ethyl acetate, tetrahydrofuran and the like.

The catalytic reduction can be carried out using the above catalyst in an amount of from about 0.05 to about 1 moles, preferably 0.1 to 0.5 moles, per mole of the carbostyril compound of the formula (II) in a solvent, for example, water or an alcohol such as methanol, ethanol or isopropanol under a hydrogen atmosphere at a pressure of from about atmospheric pressure to about 100 atmospheres, preferably atmospheric pressure to 50 atmospheres, at a temperature of from room temperature to about 150° C, preferably room temperature to 120° C, advantageously with agitating the reduction system. It is advantageous to carry out the above catalytic reduction at a temperature higher than about 50° C at atmospheric pressure or at a temperature higher than room temperature under pressure.

In the above catalytic reduction, 5-(α-substituted-aminoalkanoyl)-8-substituted-carbostyril of the formula (II) is first reduced to the compound of the formula (Ia) and then ultimately reduced to the compound of the formula (Ib), i.e., a 3,4-dihydrocarbostyril compound.

The conversion of the compound of the formula (Ia) to the compound of the formula (Ib) or vice versa can be carried out conveniently by a conventional hydrogenation or dehydrogenation, respectively, which is well known in the art.

The conversion of the compound of the formula (Ia) to the compound of the formula (Ib), i.e., hydrogenation, can be conducted in the same manner as described for the catalytic reduction of the compound of the formula (II) with hydrogen in the presence of a hydrogenation catalyst.

The conversion of the compound of the formula (Ib) to the compound of the formula (Ia), i.e., dehydrogenation, can be conducted by any known procedure which is capable of removing a hydrogen atom from each of the 3- and 4-positions of the carbostyril moiety to form a double bond between the 3- and 4-positions. This dehydrogenation can be attained by (1) a procedure using a dehydrogenating agent, for example, chloranil (tetrachloro-1,4-benzoquinone), dichlorodicyano-1,4-benzoquinone and the like; (2) a procedure using a dehydrogenating metal catalyst such as palladium black, platinum black, Raney nickel, platinum oxide and the like; or (3) a procedure using a dehydrogenating agent such as sulfur, selenium dioxide and the like. Advantageously the above procedure (1) or (2) can be used. Either of the hydrogenation or dehydrogenation can be carried out in a solvent such as aromatic hydrocarbons, for example, benzene, toluene, xylene, phenetol, chlorobenzene and the like; lower alcohols, for example, methanol, ethanol, isopropanol, tert-butanol and the like; ethers, for example, dioxane; ketones, for example, acetone and the like; water; acetic acid; etc. The dehydrogenation can be advantageously carried out at a temperature of from room temperature to the refluxing temperature of the dehydrogenation system, preferably at or near the refluxing temperature.

The compounds of the present invention having the formulae (Ia) and (Ib) wherein $R^4$ represents an alkyl group and $R^5$ represents a hydrogen atom can also be prepared by the procedures shown in Reaction Scheme III.

The carbostyril compounds of the formula (Ia) having an alkoxy group at the 8-position and a hydrogen atom at the 5-position can be prepared from the corresponding 5-($\alpha$-substituted-aminoalkanoyl)-8-alkoxycarbostyril of the formula (VIIa) by reduction with a reducing agent in the same manner as described previously for the reduction of the compound of the formula (II) shown in Reaction Scheme I. Also, the compound of the formula (Ia) having an alkoxy group at the 8-position and a hydrogen atom at the 5-position can also be prepared from the corresponding 8-hydroxy compound of the formula (VIIIa) by alkylation.

The alkylation of the compounds of the formulae (VIIIa) and (VIIIb) can be carried out by the reaction with an alkylating agent which is well known in the art in the presence of a basic compound. Suitable examples of the alkylating agent are alkyl halides such as alkyl iodides, alkyl chlorides, alkyl bromides, dialkylsulfates such as dimethyl sulfate, diethyl sulfate, etc. Suitable examples of the basic compounds are alkali metals such as sodium metal, potassium metal and the hydroxides, carbonates, bicarbonates and alcoholates thereof, aromatic amines such as pyridine, piperidine and the like.

The alkylation proceeds advantageously in a solvent such as water, lower alcohols such as methanol, ethanol, isopropanol, n-butanol, etc., and ketones such as acetone, methyl ethyl ketone and the like, using the alkylating agent in an amount of from an equimolar to a large excess of the alkylating agent, preferably 5 to 10 moles, per mole of the compound of the formula (VIIIa) or (VIIIb). The alkylation generally proceeds at room temperature.

Further, the 3,4-dihydrocarbostyril compounds of the formula (Ib) having an alkoxy group at the 8-position and a hydrogen atom at the 5-position can be prepared from the corresponding 5-($\alpha$-substituted-aminoalkanoyl)-8-alkoxy-3,4-dihydrocarbostyril of the formula (VIIb) by reduction in the same manner as described previously for the reduction of the compound of the formula (II). Either a catalytic reduction with hydrogen or a reduction with the reducing agent as described above can be employed in this reduction. Also, the compound of the formula (Ia) having an alkoxy group at the 8-position and a hydrogen atoms at the 5-position can be prepared from the corresponding 8-hydroxy compound of the formula (VIIIb) by alkylation in the same manner as described for the alkylation of the compound of the formula (VIIIa).

Alternatively, the compound of the formula (Ib) having an an alkoxy group at the 8-position and a hydrogen atom at the 5-position can be prepared from the corresponding 5-($\alpha$-substituted-aminoalkanoyl)-8-alkoxycarbostyril of the formula (VIIa) by reduction. This reduction can be carried out by the catalytic reduction with hydrogen as described for the preparation of the compound of the formula (Ib) from the compound of the formula (Ia) shown in Reaction Scheme I.

The compounds of the present invention of the formulae (Ia) and (Ib) wherein $R^2$ and $R^3$ represent hydrogen atoms can also be prepared from the compounds of the formula (II) wherein either $R^2$ or $R^3$ represents a benzyl group or an $\alpha$-methylbenzyl group. The above benzyl or $\alpha$-methylbenzyl group can easily be split off during the catalytic reduction to produce the compounds of the present invention wherein $R^2$ and $R^3$ are hydrogen atoms.

The conversion of the carbostyril of the formula (Ia) having an alkoxy group at the 8-position and a hydrogen atom at the 5-position to the 3,4-dihydrocarbostyril of the formula (Ib) having an alkoxy group at the 8-position and a hydrogen atom at the 5-position or vice versa can be carried out in the same manner as described for the conversion of the compound (Ia) to (Ib) or (Ib) to (Ia), respectively, shown in Reaction Scheme I.

The compounds used in the process shown in Reaction Scheme III as starting materials, i.e., the compounds of the formulae (VIIa), (VIIb), (VIIIa) and (VIIIb) can also be prepared in accordance with the processes described for the preparation of the compounds (Ia), (Ib), (IIa) and (IIb) in Reaction Schemes I and II using 8-hydroxy- or 8-alkoxy-carbostyril derivatives. Also, the 3,4-dihydrocarbostyril derivatives having the formulae (VIIb) and (VIIIb) can be prepared by the process disclosed in the copending application, U.S. Patent Application Ser. No. 536,516 filed Dec. 26, 1974, now U.S. Pat. No. 3,994,901.

Both the compounds of the formula (Ia) and the compounds of the formula (Ib) as obtained above are basic substances and can form acid addition salts with various organic or inorganic acids. Particularly useful such salts are the pharmaceutically acceptable acid addition salts formed with inorganic acids such as hydrochloric acid, sulfuric acid, phosphoric acid, hydrobromic acid, etc. or organic acids such as oxalic acid, maleic acid, fumaric acid, malic acid, tartaric acid, citric acid, ascorbic acid, etc. These acid addition salts can easily be prepared by well-known procedures, for example, by adding an equimolar to an excess amount of the acid to a solution of the compound of the formula (Ia) or (Ib) dissolved in an appropriate organic solvent such as methanol, ethanol, isopropanol, acetone and the like.

Both the free bases of the compounds (Ia) and (Ib) and acid addition salts thereof exhibit a stimulating acitivity on $\beta$-adrenoreceptor and, therefore, are very useful as pharmaceuticals for treating disorders such as bronchial asthma. As is apparent to one skilled in the art, the compounds of the present invention contain two asymmetrical centers and, therefore, can be present in four optically active forms. Particularly preferred compounds of the formulae (Ia) and (Ib) are the following basic compounds and their hydrochloride, sulfates, phosphates, maleates, fumarates and oxalates.

1-Methyl-5-(1-hydroxy-2-isopropylamino)ethyl-8-hydroxycarbostyril.

1-Methyl-5-(1-hydroxy-2-isopropylamino)ethyl-8-hydroxy-3,4-dihydrocarbostyril.

5-(1-Hydroxy-2-isopropylamino)ethyl-8-methoxycarbostyril.

5-(1-Hydroxy-2-isopropylamino)ethyl-8-methoxy-3,4-dihydrocarbostyril.

The present invention is further illustrated by the following Examples, but these Examples are given for illustrative purposes only and are not to be construed as limiting the scope of this invention. Unless otherwise indiated, all parts, percents, ratios and the like are by weight.

EXAMPLE 1

30 ml of nitrobenzene and 70 ml of chloroacetyl chloride (V) were added to 40 g of 1-methyl-8-methoxycarbostyril (VI), and 130 g of aluminum chloride was added slowly to the mixture while cooling with ice-water followed by allowing the mixture to react at a temperature of 60° C for 4 hours while stirring. The reaction mixture was then poured into one liter of ice-water to precipitate the product. The precipitate was filtered, washed with diethyl ether and recrystallized from a mixture of chloroform and ethanol (2:5 by volume) to obtain 32 g of white amorphous 1-methyl-5-chloroacetyl-8-methoxycarbostyril (IV) having a melting point of 204 to 205.5° C. The product thus obtained was confirmed by elemental analysis and IR and NMR spectral analyses.

EXAMPLE 2

40 ml of nitrobenzene and 12 ml of monochloroacetyl chloride (V) were added to 7.4 g of 1-methyl-8-hydroxycarbostyril (VI), and 20 g of aluminum chloride was added slowly to the mixture while cooling with ice-water followed by allowing the mixture to react at a temperature of 60° C for 18 hours while stirring. The reaction mixture was then poured into 500 ml of ice-water to precipitate the product. The precipitate was filtered, washed with diethyl ether and recrystallized from a mixture of ethanol and dimethylformamide (1:1 by volume) to obtain 2.8 g of white amorphous 1-methyl-5-chloroacetyl-8-hydroxycarbostyril (IV) having a melting point of 287 to 289° C (with decomposition). The product thus obtained was confirmed by elemental analysis and IR and NMR spectral analyses.

EXAMPLE 3

2.7 g of 1-methyl-5-chloroacetyl-8-methoxycarbostyril (IV) prepared as described in Example 1 was dissolved in 40 ml of isopropanol, and 9 g of isopropylamine (III) was added to the solution while heating the solution at a temperature of 55° to 60° C over a period of 1.5 hours. After completion of the addition, the mixture was allowed to react for one hour while stirring. The reaction mixture was concentrated under reduced pressure and the resulting residue was dissolved in 40 ml of isopropanol. The solution was then filtered to remove any insoluble material, and the filtrate was adjusted to a pH of 2–3 with concentrated hydrochloric acid. The mixture was cooled with ice and the precipitate formed was filtered and recrystallized from ethanol to obtain 0.4 g of white amorphous 1-methyl-5-isopropylaminoacetyl-8-methoxycarbostyril (IIb) hydrochloride. The product thus obtained was confirmed by elemental analysis and IR spectral analysis.

EXAMPLE 4

10 ml of isopropanolamine (III) was added to 1.6 g of 1-methyl-5-chloroacetyl-8-hydroxycarbostyril (IV) prepared as described in Example 2, and the mixture was allowed to react at a temperature of 35° C for 2 hours while stirring. The reaction mixture was concentrated under reduced pressure, and the residue was distilled azeotropically with ethanol to dryness. The resulting residue was dissolved in 20 ml of ethanol, and the solution was filtered to recover the insoluble material which was then dissolved in hot ethanol. The solution was adjusted to a pH of 2–3 with concentrated hydrochloric acid and cooled with ice. The precipitate formed was filtered and dissolved in 20 ml of water. The solution was adjusted to a pH of 6.5–7.5 with sodium bicarbonate and the precipitate formed was filtered and recrystallized from ethanol to obtain 1.1 g of white amorphous 1-methyl-5-isopropylaminoacetyl-8-hydroxycarbostyril (IIa) having a melting point of 136° to 138° C (with decomposition).

EXAMPLE 5

2.0 g of 1-methyl-5-isopropylaminoacetyl-8-methoxycarbostyril (IIb) hydrochloride prepared as described in Example 3 was dissolved in 30 ml of a 47% aqueous solution of hydrobromic acid, and the solution was heated in an oil bath at a temperature of 120° to 130° C for 8 hours under refluxing. 10 ml of water was then added to the reaction mixture followed by concentration by distillation. 10 ml of water was again added to the mixture followed by concentration. After allowing the mixture to cool, the precipitate formed was filtered and dissolved in 60 ml of water by heating. The resulting solution was adjusted to a pH of 6.5–7.5 with sodium bicarbonate and the precipitate formed was filtered. Recrystallization of the precipitate from ethanol yielded 0.45 g of white amorphous 1-methyl-5-isopropylaminoacetyl-8-hydroxycarbostyril (IIa) having a melting point of 136° to 138° C (with decomposition). The product thus obtained was confirmed by elemental analysis and IR and NMR spectral analyses.

EXAMPLE 6

0.45 g of 1-methyl-5-isopropylaminoacetyl-8-hydroxycarbostyril (IIa) was dissolved in 50 ml of methanol, and 0.2 g of sodium borohydride was added slowly to the solution while ice-cooling and stirring. The stirring was further continued for an additional hour and the resulting reaction mixture was adjusted to a pH of 2–3 with concentrated hydrochloric acid. The precipitate formed was then removed by filtration. The filtrate was concentrated under reduced pressure, and the residue was dissolved in 20 ml of ethanol. The solution was filtered to remove any insoluble material. The filtrate was concentrated under reduced pressure and 20 ml of ethanol was added thereto followed by filtration to remove any insoluble material. The filtrate was concentrated under reduced pressure to dryness and 40 ml of ethanol was added to the residue to remove any ethanol-soluble material remaining in the residue. The ethanol-insoluble material was washed twice with 20 ml portions of cold water and recrystallized from ethanol to obtain 0.3 g of white amorphous 1-methyl-5-(1-hydroxy-2-isopropylamino)ethyl-8-hydroxycarbostyril (Ia) hydrochloride having a melting point of 202° to 203.5° C (with decomposition). The product thus obtained was confirmed by IR and NMR spectral analyses and elemental analysis.

EXAMPLE 7

1 g of 1-methyl-5-isopropylaminoacetyl-8-hydroxycarbostyril (IIa) hydrochloride was suspended in 100 ml of water, and 0.1 g of palladium black and 0.1 g of palladium-on-carbon were added to the suspension followed by catalytically reducing the mixture with hydrogen at atmospheric pressure at a temperature of 60 to 70° C for 25 hours. After completion of the reduction, the reaction mixture was filtered, and the filtrate was concentrated to dryness under reduced pressure. The resulting residue was crystallized from acetone and then recrystallized from ethanol to obtain 0.3 g of white amorphous 1-methyl-5-(1-hydroxy-2-isopropylamino)ethyl-8-hydroxy-3,4-dihydrocarbostyril (IIb) having a melting point of 196° to 197° C (with decomposition). The product thus obtained was confirmed by IR and NMR spectral analyses and elemental analysis.

EXAMPLE 8

1.0 g of 5-isopropylaminoacetyl-8-methoxycarbostyril (IIb) was dissolved in 50 ml of methanol, and 0.6 g of sodium borohydride was added slowly to the solution while ice-cooling and stirring followed by stirring the mixture at room temperature for one hour. The reaction mixture was adjusted to a pH of 2–3 with concentrated hydrochloric acid, and the precipitate formed was filtered. The filtrate was concentrated to dryness and crystallized from acetone. Recrystallization of the product from ethanol yielded 0.8 g of a material having a melting point of 230° to 231° C (with decomposition). The product thus obtained was confirmed by NMR and IR spectral analyses and elemental analysis to be 5-(1-hydroxy-2-isopropylamino)ethyl-8-methoxy-3,4-dihydrocarbostryril (Ia) hydrochloride monohydrate.

EXAMPLE 9

2 g of 5-isopropylaminoacetyl-8-methoxy-3,4-dihydrocarbostyril (VIIb) was dissolved in 70 ml of methanol, and 1 g of sodium borohydride was added slowly to the solution while cooling with ice-water followed by stirring at room temperature for an additional hour. The reaction mixture was adjusted to a pH of 1 with concentrated hydrochloric acid, and the precipitate formed was filtered. The filtrate was concentrated to dryness and the resulting residue was recrystallized from ethanol to obtain 1.5 g of a material having a melting point of 206° to 208° C (with decomposition). The product thus obtained was confirmed by NMR and IR spectral analyses and elemental analysis to be 5-(1-hydroxy-2-isopropylamino)ethyl-8-methoxy-3,4-dihydrocarbostyril (Ib) hydrochloride.

EXAMPLE 10

3 g of 5-(1-hydroxy-2-isopropylamio)ethyl-8-hydroxycarbostyril (VIIIa) hydrochloride was dissolved in 20 ml of water, and 0.9 g of sodium hydroxide was added to the solution. 1.3 g of dimethyl sulfate was then added dropwise to the solution while ice-cooling and stirring over a period of one hour. The mixture was stirred for 2 hours at a temperature of 40° to 50° C, and the reaction mixture was extracted with chloroform. The chloroform extract was washed with water and dried, and hydrogen chloride gas was introduced into the chloroform extract. The precipitated crystals were recrystallized from a mixture of ethanol and acetone to obtain 2.3 g of a material having a melting point of 235° to 237° C (with decomposition). The product thus obtained was confirmed by NMR and IR spectral analyses and elemental analysis to be 5-(1-hydroxy-2-isopropylamino)ethyl-8-methoxycarbostyril (Ia) hydrochloride monohydrate.

EXAMPLE 11

2.6 g of 5-(1-hydroxy-2-isopropylamino)ethyl-8-hydroxy-3,4-dihydrocarbostyril (VIIIb) was dissolved in 30 ml of water and 0.45 g of sodium hydroxide was added to the solution. 1.3 g of dimethylsulfate was then added dropwise to the solution while ice-cooling and stirring over a period of one hour. The reaction mixture was stirred for 2 hours at a temperature of 10° to 50° C and extracted with chloroform. The chloroform extract was washed with water and dried, and hydrogen chloride gas was introduced into the chloroform extract. The precipitated crystals were recrystallized from ethanol to obtain 2.2 g of a material having a melting point of 206° to 208° C (with decomposition). The product thus obtained was confirmed by NMR and IR spectral analyses and elemental analysis to be 5-(1-hydroxy-2-isopropylamino)ethyl-8-methoxy-3,4-dihydrocarbostyril hydrochloride (Ib).

EXAMPLE 12

10 ml of a 47% aqueous hydrobromic acid was added to 1 g of 1-methyl-5-(1-hydroxy-2-isopropoylamino)ethyl-8-methoxy-3,4-dihydrocarbostyril (VIIb) hydrochloride monohydrate, and the mixture was heated under refluxing for 15 hours followed by concentration to dryness. Acetone was added to the resulting residue to crystallize the product which was then adjusted to a pH of 8 with a dilute aqueous sodium hydroxide solution. The precipitated crystals were filtered, washed with water and dissolved in ethanol. The solution was adjusted to a pH 1 with concentrated hydrochloric acid and concentrated to dryness. The residue thus obtained was recrystallized from a mixture of ethanol and diethyl ether to obtain 0.7 g of a material having a melting point of 198° to 200° C (with decomposition). The product thus obtained was confirmed by NMR and IR spectral analyses and elemental analysis to be 1-methyl-5-(1-hydroxy-2-isopropylamino)-ethyl-8hydroxy-3,4-dihydrocarbostyril (Ib) hydrochloride.

REFERENCE EXAMPLE

The stimulating activity of the compounds of this invention on β-adreno-receptor was determined as follows:

Male hydrid adult dogs, weighing 10 to 15 Kg were anesthesized with 30 mg/Kg of body weight of sodium pentobarbital administered intravenously. Each of the anesthesized dogs was secured on its back and a cannula was inserted into the trachea. Artificial respiration was conducted using a device according to the Konzett-Rossler method (Konzett H. & Rossler R., "Versuchsanordnug zu Untersuchungen an der Bronchial Moskolatur", Arch. Exp. Path., Pharmack, 195, 71–74, 27–40 (1940)). The volume of the overflowing air at the time of inhalation was measured through a pneumotachometer to determine bronchial resistance and the values obtained were recorded on a polygraph.

In the above experiment, histamine was employed as a bronchoconstrictor at a dosage level of 10 mg/Kg of body weight, and an aqueous solution containing each of the test compounds and controls shown in Table I below was then administered to each of the anesthisized dogs through the femoral vein at the various dosage levels as shown in Table I below 1 minute before the administration of the histamine. Sodium pentobarbital was infused during the experiment at a dosage level of 4 mg/Kg of body weight/hr. using an automatic injector in order to inhibit spontaneous respiration and to keep the anesthetic condition constant over the test period. The results obtained are shown in Table I below.

Table I

| Compound | Bronchial Resistance (%) Dosage Level(μg/Kg) | | | | | | | | |
|---|---|---|---|---|---|---|---|---|---|
| | 0.01 | 0.03 | 0.1 | 0.3 | 1.0 | 3.0 | 10 | 30 | 100 |
| 1-Methyl-5-(1-hydroxy-2-isopropylamino)-ethyl-8-hydroxy-carbostyril Hydrochloride | 0 | 0 | 0 | 5.2 | 16.8 | 36.5 | — | — | — |
| 5-(1-Hydroxy-2-isopropylamino)-ethyl-8-methoxy-carbostyril Hydrochloride Monohydrate (control) | 0 | 0 | 0 | 0 | 8.2 | 17.9 | — | — | — |
| Isoproterenol | 0 | 16.6 | 58.3 | 83.3 | 100 | — | — | | |
| Salbutamol | 0 | 0 | 16.6 | 33.3 | 66.6 | 100 | | | |
| Metaproterenol Sulfate (Arotec) | 0 | 0 | 2.7 | 11.1 | 27.5 | 50.0 | 88.3 | 100 | |
| Quinterenol | 0 | 0 | 0 | 0 | 0 | 0 | 0 | 7.6 | 15.3 |

Further, the acute toxicity was determined with respect to the test compounds shown in Table II below using 5 to 6 groups each containing 10 male rats (dd strain; body weight, 18 to 22g) which had been fasted for 12 hours prior to the test. Salbutamol and Isoproterenol were used as a control. The $LD_{50}$ (50% lethal dose) results are as follows.

Table II

| Compound | $LD_{50}$ (mg/Kg) | |
|---|---|---|
| | i.v. | p.o. |
| 1-Methyl-5-(1-hydroxy-2-isopropylamino)ethyl-8-hydroxycarbostyril Hydrochloride | 46.5 (40.1–51.8) | 750 (523–1147) |
| 5-(1-Hydroxy-2-isopropylamino)ethyl-8-methoxycarbostyril Hydrochloride | 86.3 (65.3–103.7) | 830 (473–1371) |
| Salbutamol | 57.1 (52.7–61.9) | 4620* (4160–5130)* 660 (412.5–1056) |
| Isoproterenol | 112.5 (87.9–144.0) | 2587* 355 (235.1–536.1) |

* Literature values

The compounds of the present invention can be administered at a dosage level of from 100 γ to 50 mg/kg/day by oral, intravenous, intramuscular, intrarectal or inhalation administration in a conventional pharmaceutical dosage form such as a tablet, powder, granule, capsule, syrup, solution, suspension, inhalant (aerosol spray), suppository and the like, preferably, in combination with pharmaceutically acceptable carriers or diluents which are well known in the art.

Pharmaceutical compositions generally comprise at least one compound of the present invention and pharmaceutical carriers or diluents which are commonly employed in conventional pharmaceutical compositions. The composition may contain other active components which do not adversely affect the activities of the compound of this invention.

Suitable pharmaceutical carriers or diluents include solid carriers such as corn starch, calcium sulfate dihydrate, magnesium stearate, lactose, Aerosil (tradename of Nihon Aerosil Co., Ltd. Japan) and the like which are suitable for use in oral, suppository, injectable and inhalant formulations. The oral dosage forms can be formulated in accordance with well known procedures and conveniently formulated into tablets which can be optionally provided with a sugar coating. A soluble tablet which is suitable for sublingual administration, i.e., troche or lozenge, can also be prepared.

The injectable composition can be prepared using physiologically acceptable carriers or diluents in the form of a solution, suspension or dry preparation which is reconstituted instantaneously with a vehicle for injection just before administration.

The compounds of the present invention are advantageously administered in the form of an aerosol spray formulation by inhalation.

Typical examples of suitable formulations are given below, but it is to be noted that other dosage forms can also be prepared using other compounds of this invention according to the well-established pharmaceutical techniques.

Formulation 1

Tablets each containing the following components were prepared from the following components:

| Components | Amount |
|---|---|
| 1-Methyl-5-(1-hydroxy-2-isopropylamino)-ethyl-8-hydroxycarbostyril | 1 mg |
| Corn Starch | 70 mg |
| Magnesium stearate | 9 mg |
| Lactose | 20 mg |
| Total | 100 mg |

Formulation 2

Aerosol spray for inhalation containing the following components per each dose was prepared and filled in the aerosol dispenser:

| Components | Amount |
|---|---|
| 1-Methyl-5-(1-hydroxy-2-isopropylamino)ethyl-8-hydroxycarbostyril | 50 mcg |
| Oleic Acid | 10 mcg |
| Dichlorodifluoromethane | 57 mg |
| Trichlorofluoromethane | 25 mg |

While the invention has been described in detail and with reference to specific embodiments thereof, it will be apparent to one skilled in the art that various changes and modifications can be made therein without departing from the spirit and scope thereof.

What is claimed is:

1. A 5-[1-hydroxy-2-(substituted-amino)] alkyl-8-substituted-carbostyril or 5-[1-hydroxy-2-(substituted-amino)] alkyl-8-substituted-3,4-dihydrocarbostyril compound represented by the formula (Ia) or (Ib)

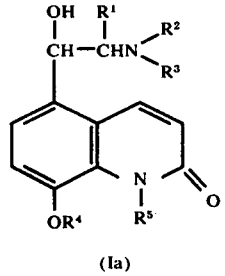 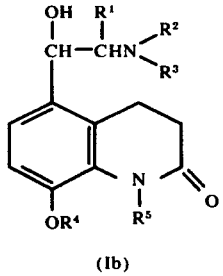

(Ia)          (Ib)

wherein $R^1$, $R^4$ and $R^5$ each represents a hydrogen atom or an alkyl group having 1 to 3 carbon atoms, with at least one of $R^4$ and $R^5$ being an alkyl group, and $R^2$ and $R^3$, which may be the same or different, each represents a hydrogen atom, an alkyl group having 1 to 4 carbon atoms, a phenyl alkyl group having a straight or branched chain alkyl moiety having 1 to 4 carbon atoms or a cycloalkyl group having 4 to 6 carbon atoms, $R^2$ and $R^3$ may, when taken together with the nitrogen atom to which they are attached, form a 5- or 6-membered heterocyclic ring which is unsubstituted or substituted with an alkyl group having 1 to 4 carbon atoms, said heterocyclic ring being selected from the group consisting of pyrrolidino, piperidino, morpholino, and piperazino, and the pharmaceutically acceptable acid addition salts thereof.

2. A 5-[1-hydroxy-2-(substituted-amino)]alkyl-8-substituted carbostyril or 5-[1-hydroxy-2-(substituted-amino)]alkyl-8-substituted-3,4-dihydrocarbostyril compound represented by the formula (Ia) or (Ib)

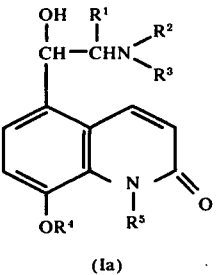 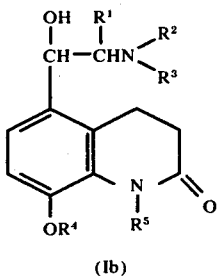

(Ia)          (Ib)

wherein $R^1$, $R^4$ and $R^5$ each represents a hydrogen atom or an alkyl group having 1 to 3 carbon atoms, with at least one of $R^4$ and $R^5$ being an alkyl group, and $R^2$ and $R^3$, which may be the same or different, each represents a hydrogen atom, an alkyl group having 1 to 4 carbon atoms, a phenyl alkyl group having a straight or branched chain alkyl moiety having 1 to 4 carbon atoms or a cycloalkyl group having 4 to 6 carbon atoms, $R^2$ or $R^3$ may, when taken together with the nitrogen atom to which they are attached, form a 5- or 6-membered heterocyclic ring which is unsubstituted or substituted by an alkyl group having 1 to 4 carbon atoms, said heterocyclic ring being selected from the group consisting of pyrrolidino, and piperidino and the pharmaceutically acceptable acid addition salts thereof.

3. 1-Methyl-5-(1-hydroxy-2-isopropylamino)ethyl-8-hydroxycarbostyril according to claim 2.

4. 1-Methyl-5-(1-hydroxy-2-isopropylamino)ethyl-8-hydroxy-3,4-dihydrocarbostyril according to claim 2.

5. 5-(1-Hydroxy-2-isopropylamino)ethyl-8-methoxycarbostyril according to claim 2.

6. 5-(1-Hydroxy-2-isopropylamino)ethyl-8-methoxy-3,4-dihydrocarbostyril according to claim 2.

* * * * *